US008728982B2

(12) United States Patent
Wang et al.

(10) Patent No.: US 8,728,982 B2
(45) Date of Patent: *May 20, 2014

(54) ENGINEERED HYBRID PHAGE VECTORS FOR THE DESIGN AND THE GENERATION OF A HUMAN NON-ANTIBODY PEPTIDE OR PROTEIN PHAGE LIBRARY VIA FUSION TO PIX OF M13 PHAGE (75) Inventors: Bryan Wang, Wyomissing, PA (US); Linus Hyun, Radnor, PA (US); Karyn O'Neil, Radnor, PA (US)

(73) Assignee: Centoco Ortho Biotech Inc., Horsham, PA (US)

( * ) Notice: Subject to any disclaimer, the term of this patent is extended or adjusted under 35 U.S.C. 154(b) by 461 days.

This patent is subject to a terminal disclaimer.

(21) Appl. No.: 12/743,249

(22) PCT Filed: Nov. 21, 2008

(86) PCT No.: PCT/US2008/084281
§ 371 (c)(1),
(2), (4) Date: May 17, 2010

(87) PCT Pub. No.: WO2009/085464
PCT Pub. Date: Jul. 9, 2009

(65) Prior Publication Data
US 2010/0249377 A1 Sep. 30, 2010

(51) Int. Cl.
C40B 40/08 (2006.01)
(52) U.S. Cl.
USPC .......................................................... 506/17
(58) Field of Classification Search
None
See application file for complete search history.

(56) References Cited

U.S. PATENT DOCUMENTS

| 2002/0068272 A1 | 6/2002 | Larocca et al. |
| 2003/0104355 A1* | 6/2003 | Wang et al. ........................ 435/5 |
| 2003/0186322 A1 | 10/2003 | Janda et al. |
| 2008/0287304 A1 | 11/2008 | Paschke |

FOREIGN PATENT DOCUMENTS

| EP | 1 536 005 A1 | 6/2005 |
| WO | WO 94/17101 A1 | 8/1994 |
| WO | WO 00/71694 A1 | 11/2000 |
| WO | WO 2004/050871 A1 | 6/2004 |
| WO | WO 2009/024591 A1 | 2/2009 |

OTHER PUBLICATIONS

Pini et al. (Aug. 21, 1998) The Journal of Biological Chemistry vol. 273 pp. 21769 to 21776.*
Kehoe, J. W., and B. K. Kay. 2005. Filamentous phage display in the new millennium. Chem Rev 105:4056.
Iannolo, G., O. Minenkova, R. Petruzzelli, and G. Cesareni. 1995. Modifying filamentous phage capsid: limits in the size of the major capsid protein. J Mol Biol 248:835.
Gao, C., S. Mao, C. H. Lo, P. Wirsching, R. A. Lerner, and K. D. Janda. 1999. Making artificial non-antibody peptides or proteins: a format for phage display of combinatorial heterodimeric arrays. Proc Natl Acad Sci U S A 96:6025.

(Continued)

Primary Examiner — Christian Boesen
(74) Attorney, Agent, or Firm — Brian C. Carey (57) ABSTRACT The invention relates to a compositions and methods for generating and using pIX phage display libraries for producing non-antibody peptide or protein proteins or peptides using engineered hybrid phage vectors derived from pIX of M 13 phage 12 Claims, 6 Drawing Sheets (56) References Cited

OTHER PUBLICATIONS

Gao, C., S. Mao, G. Kaufmann, P. Wirsching, R. A. Lerner, and K. D. Janda. 2002. A method for the generation of combinatorial antibody libraries using pIX phage display. Proc Natl Acad Sci U S A 99:12612.

Gao, C., S. Mao, H. J. Ditzel, L. Farnaes, P. Wirsching, R. A. Lerner, and K. D. Janda. 2002. A cell-penetrating peptide from a novel pVII-pIX phage-displayed random peptide library. Bioorg Med Chem 10:4057.

Endemann, H., and P. Model. 1995. Location of filamentous phage minor coat proteins in phage and in infected cells. J Mol Biol 250:496.

Kwasnikowski, P., P. Kristensen, and W. T. Markiewicz. 2005. Multivalent display system on filamentous bacteriophage pVII minor coat protein. J Immunol Methods 307:135.

Hill, D. F., and G. B. Petersen. 1982. Nucleotide Sequence of Bacteriophage f1 DNA. Journal of Virology 44:32-46.

Sidhu et al., High Copy Display of Large Proteins on Phage for Functional Selections, Journal of Molecular Biology, vol. 296, No. 2, 2005, pp. 487-495.

International Search Report PCT/US08/84281 dated May 19, 2009.

Supplementary European Search Report for EP2238246 published Oct. 13, 2010 dated Jun. 6, 2012.

\* cited by examiner

```
                                                                Shine-Dalgarno                    PelB leader
                                                    HindIII
                                                                          Met Lys Tyr Leu Leu Pro Thr Ala Ala Ala
TTGTGAGCGG ATAACAATTT CACACAGGAA ACAGCTATGA CCATGATTAC GCCAAGCTTA GGAGGACAGC TATGAAATAC CTATTGCCTA CGGCAGCCGC
AACACTCGCC TATTGTTAAA GTGTGTCCTT TGTCGATACT GGTACTAATG CGGTTCGAAT CCTCCTGTCG ATACTTTATG GATAACGGAT GCCGTCGGCG
                     PelB leader                              FLAG tag                  BbsI          pIX coat protein
Ala Gly Leu Leu Leu Leu Ala Ala Gln Pro Ala Met Ala   Asp Tyr Lys Asp Asp Asp Lys Gly Gly Thr Lys Thr Met Ser Val Leu Val Tyr
TGGATTGTTA TTACTCGCGG CCCAGCCGGC CATGGCCGTC TTCGACTATA AGGATGATGA CGACAAAGGC GGTACGAAGA CGATGAGTGT TTTAGTGTAT
ACCTAACAAT AATGAGCGCC GGGTCGGCCG GTACCGGCAG AAGCTGATAT TCCTACTACT GCTGTTTCCG CCATGCTTCT GCTACTCACA AAATCACATA
                                                BbsI
                               pIX coat protein                                                    trp A terminator
Ser Phe Ala Ser Phe Val Leu Gly Trp Cys Leu Arg Ser Gly Ile Thr Tyr Phe Thr Arg Leu Met Glu Thr Ser Ser *** *** Thr
TCTTTCGCCT CTTTCGTTTT AGGTTGGTGC CTTCGTAGTG GCATTACGTA TTTTACCCGT TAATGGAAA CTTCCTCATA ATGAACTCAG ATACCCAGCC
AGAAAGCGGA GAAAGCAAAA TCCAACCACG GAAGCATCAC CGTAATGCAT AAAATGGGCA AATTACCTTT GAAGGAGTAT TACTTGAGTC TATGGGTCGG
       trp A terminator
                            EcoRI
CGCCTAATGA GCGGGCTTTT TTTTGAATTC ACTGGCCGTC GTTTTACAAC GTCGTGACTG GGAAAACCCT GGCGTTACCC AACTTAATCG CCTTGCAGCA
GCGGATTACT CGCCCGAAAA AAAACTTAAG TGACCGGCAG CAAAATGTTG CAGCACTGAC CCTTTTGGGA CCGCAATGGG TTGAATTAGC GGAACGTCGT
```

ENGINEERED HYBRID PHAGE VECTORS FOR THE DESIGN AND THE GENERATION OF A HUMAN NON-ANTIBODY PEPTIDE OR PROTEIN PHAGE LIBRARY VIA FUSION TO PIX OF M13 PHAGE

CROSS-REFERENCE TO RELATED APPLICATIONS

This application claims the benefit of International Application Number PCT/US2008/084281, filed 21 Nov. 2008, which claims the benefit of U.S. Provisional Application Number 61/014,773, filed 19 Dec. 2007. The entire contents of each of the aforesaid applications are incorporated herein by reference in their entirety.

FIELD OF THE INVENTION

The invention relates to a compositions and methods for generating and using pIX phage display libraries for producing non-antibody peptide or protein proteins or peptides using engineered hybrid phage vectors derived from pIX of M13 phage.

BACKGROUND OF THE INVENTION

Phage display is a well-established tool for affinity-based selection of polypeptides. In a typical phage display selection, a library of polypeptides is genetically fused to the terminus of one of the coat proteins of the filamentous phage M13. The phage particle provides a physical link between each polypeptide member of the library and the gene that encodes it. The phage library can then be affinity-selected, or panned, for those members of the library that bind to a desired target molecule. The library is mixed with the target, unbound phage particles are washed away, and the remaining phage eluted and amplified by culturing in E. coli cells.

Although the display of foreign polypeptides has been accomplished with each of the coat proteins of M13, pIII and pVIII are by far the most common fusion partners. pIII is a 42 kD minor coat protein that is responsible for phage infection into E. coli. Each phage particle contains up to five copies of the pIII protein on its surface, gathered at one end of the phage. PVIII is the major coat protein of the phage; thousands of copies of pVIII (molecular weight 5 kD) are arranged in an orderly fashion around the single-stranded viral genome to comprise the phage capsid. In addition to pIII, M13 has three other minor coat proteins: pVI, a 12 kD protein, and pVII and pIX, which are short proteins (33 and 32 amino acids, respectively) that are involved in initiation of assembly and maintenance of stability. Five copies of the pVI protein lie at the same end of the phage as pIII, while five copies each of pVII and pIX reside at the opposite end of the phage.

While phage libraries displaying fusions to pIII and pVIII have proven productive in many cases, the polypeptides displayed by phage are subject to certain biological constraints. For instance, most peptides of eight or more amino acids in length do not display well as fusions to pVIII. In addition, polypeptides that interact with the phage protein itself or otherwise affect the expression, incorporation, or activity of pIII or pVIII will be under-represented in the library, because the phage that display them will not grow well. Finally, because pIII is a rather large protein, access of pIII-displayed polypeptides to certain target sites (deep, narrow crevices on a protein surface, for instance), or the correct assembly of polypeptides that function best in multimeric form, might be sterically hindered. Thus, selections from phage libraries that exploit other coat proteins—which have different structures and biological functions and thus might be expected to impose different constraints on displayed polypeptides would help to ensure that a maximum amount of sequence diversity is searched. In proof of concept experiments, it has been shown that pVII and pIX can be used for the display of both antibody fragments and peptides. These results were especially noteworthy since earlier work had suggested that fusions of polypeptides to the N-termini of pVII and pIX render these coat proteins non-functional.

The display of foreign polypeptides on phage is accomplished through the use of phage, phagemid, or hybrid vectors. With phage vectors, the gene of interest is introduced into the phage genome as an in-frame fusion with the native coat protein gene. These vectors propagate independently as fully functional phage and display multiple copies of the foreign polypeptide. Phagemid vectors, in contrast, are plasmids that contain a phage origin of replication and packaging signal in addition to a bacterial origin of replication. Phagemids carry the gene of interest fused to a recombinant copy of the coat protein gene and, upon rescue with a helper phage, are packaged into progeny virus with the displayed polypeptide incorporated into the phage coat. The requirement for helper phage causes phagemid vectors to be more labor-intensive than phage vectors, and complicates efforts to quantitate the number of phage that are present in any given sample. Furthermore, since phage particles can draw upon both wild-type coat proteins and fusion coat proteins for assembly, some proportion of the resultant phage will not display the polypeptide sequence of interest, resulting in low display efficiency. Hybrid vectors resemble phage vectors in that the fusion protein is carried in the phage genome and no helper phage are needed, but they also resemble phagemid systems in that the genome also carries a wild-type copy of the fusion protein. Previous reports of pIX phage display describe fusions in the context of phagemid vectors; display of polypeptides on pIX from a hybrid or phage vector has not previously been reported. Display of polypeptides on pVII from a phage vector has recently been reported.

There is a need for providing synthetic non-antibody peptide or protein libraries and methods that simultaneously deliver the critical elements of human therapeutic peptides and proteins of high affinity and activity, high productivity, good solution properties, and a propensity of low immune response when administered in man. There is a further need to increase the efficiency of non-antibody peptide or protein isolation from synthetic libraries, relative to current methods, to reduce the resource costs of non-antibody peptide or protein discovery and accelerate delivery of non-antibody peptides or proteins for biological evaluation. The libraries and methods of this invention meet these needs by coupling comprehensive design, assembly technologies, and phage pIX Peptide or protein display.

SUMMARY OF THE INVENTION

The present invention provides engineered pIX phage vectors that can be used with pVII and pIX phage display for generating peptide or protein libraries using pIX from M13 phage, e.g., using mutagenesis or other diversity producing techniques, optionally with in line maturation, to provide an efficient and fast platform for peptide or protein and non-antibody peptide or protein fragment generation and selection of therapeutic non-antibody peptides or proteins. According to the present invention, hybrid phage vectors are provides that have been engineered to include a second recombinant pIX coding region linked to an upstream signal peptide and inducible promoter.

The present invention provides a hybrid vector for the display of peptides and proteins as fusions to pIX or pVII phage proteins for use in expressing such peptides or proteins as peptide or protein libraries for use, e.g., but not limited to screening, selection, engineering, maturation or other uses, e.g., providing potential therapeutic or diagnostic peptides or proteins. Because the regulatory and coding regions of the native gene IX overlap those of pVII and pVIII, simple fusions to the terminus of this gene would likely inactivate the phage (Hill and Petersen, J. of Virol. 44:32-46, 1982). Instead, a derivative of M13mp19 has been engineered to include a second recombinant pIX coding region linked to an upstream signal peptide and inducible promoter. The use of this vector, rather than a phagemid, obviates the need for helper phage and significantly reduces the amount of time and effort needed to culture the phage during selection and analysis. Furthermore, the number of phage grown with this vector can be determined more easily than the number of phage grown from a phagemid.

Thus the invention provides a novel vector construct for use in expressing peptides or proteins in a pIX phage display format for construction of polypeptide arrays. In particular, the invention describes an engineered pIX phage vector that includes a second recombinant pIX coding sequence encoding a fusion polypeptide, wherein the fusion polypeptide comprises an exogenous polypeptide fused to the amino terminus of a filamentous phage pVII or pIX protein. Preferably, the phage particle comprises the expressed fusion protein on the surface of the phage particle.

In aspect, the present invention provides an engineered recombinant nucleic acid phage vector for expressing phage display fusion peptides or proteins that bind to selected biologically active ligands, comprising (a) a recombinant phage leader coding nucleic acid sequence; operably linked to: (b) a recombinant tag, promoter, or selection coding nucleic acid sequence; operably linked to: (c) a recombinant pIX or pVII encoding nucleic acid sequence; operably linked to: (d) a recombinant restriction site; operably linked to: (e) a peptide linker encoding nucleic acid sequence; operably linked to a: (f) a first exogenous peptide or protein encoding sequence that selectively binds to a biologically active ligand; (g) a pVII encoding nucleic acid sequence; (h) a native pIX encoding nucleic acid sequence; (i) a pIII encoding nucleic acid sequence; and (j) a pVI encoding nucleic acid sequence.

Such an engineered nucleic acid phage vector can include wherein said phage leader coding sequence is a pelB sequence. Such an engineered nucleic acid phage vector can include wherein recombinant tag or selection sequence is a FLAG tag sequence. Such an engineered nucleic acid phage vector can include wherein recombinant tag or selection sequence is selected from SEQ ID NOS:3, 4, 5, or 6. Such an engineered nucleic acid phage vector can include wherein said FLAG tag sequence comprises SEQ ID NO:2. Such an engineered nucleic acid phage vector can include wherein said promoter is an inducible promoter. Such an engineered nucleic acid phage vector can include wherein said inducible promoter is a lac promoter. Such an engineered nucleic acid phage vector can include wherein said peptide linker is selected from SEQ ID NOS:7 and 8. Such an engineered nucleic acid phage vector can include wherein said exogenous first peptide or protein is a putative biologically active proteins or peptides. Such an engineered nucleic acid phage vector can include wherein said biologically active ligands mediate at least one biological in vivo activity. Such an engineered nucleic acid phage vector can include wherein said vector encodes a second exogenous peptide or protein fused to at least one phage coat protein.

The invention also includes a bacterial host cell comprising an engineered nucleic acid phage vector. The host cell can express a biologically active fusion protein.

The invention also relates to a biologically active fusion protein expressed by a bacterial host cell according to the invention. The invention also relates to a biologically active exogenous peptide or protein derived from said fusion protein.

The invention also relates to a phage library of bacterial host cells comprising a plurality of engineered nucleic acid phage vectors according to the present invention. The phage library can include wherein variants of said exogenous first peptides or proteins are expressed.

The invention also provides a method for screening a phage peptide or protein library for exogenous peptide or proteins having a desired biological activity, comprising (a) expressing exogenous peptides or proteins from a phage library, and (b) selecting bacterial cells expressing an exogenous peptide or protein having said desired biological activity. The invention also provides an exogenous peptide or protein encoding nucleic acid, obtained from such a method.

In one embodiment, the phage vector further encodes a second fusion polypeptide, wherein the second fusion polypeptide comprises a second exogenous polypeptide fused to the amino terminus of the pIX or pVII protein and the first exogenous polypeptide in the first fusion polypeptide is fused to the amino terminus of the pIX or pVII protein. In one embodiment, the first and second fusion polypeptides can associate to form a heterodimeric protein complex, such as a target protein, a receptor, a nucleic acid binding protein or an enzyme.

In another embodiment, the invention describes a vector for expressing a fusion protein on the surface of a filamentous phage comprising a cassette for expressing the fusion protein. The cassette includes upstream and downstream translatable DNA sequences operatively linked via a sequence of nucleotides adapted for directional ligation of an insert DNA, i.e., a polylinker, where the upstream sequence encodes a prokaryotic secretion signal, the downstream sequence encodes a pVII or pIX filamentous phage protein. The translatable DNA sequences are operatively linked to a set of DNA expression signals for expression of the translatable DNA sequences as portions of the fusion polypeptide. In a preferred variation, the vector optionally further comprises a second cassette for expressing a second fusion protein on the surface of the filamentous phage, wherein the second cassette has the structure of the first cassette with the proviso that the first fusion protein expression cassette encodes pIX or pVII protein and/or the second fusion protein expression cassette encodes pIX or pVII protein. The vector is used as a phage genome to express heterodimeric protein complexes on the surface of the phage particle in which the two exogenous polypeptides of the heterodimer are anchored on the phage particle by the fusion to the first and second phage proteins, pVII and/or pIX.

In another embodiment, the invention contemplates a library of phage particles according to the present invention, i.e., a combinatorial library, based on the engineered pIX phage vector in which representative particles in the library each display a different fusion protein. Where the particle displays a heterodimeric protein complex, the library comprises a combinatorial library of heterodimers, such as non-antibody peptides or proteins in the form of a library of Fv molecules. Preferred libraries have a combinatorial diversity of at least $10^3$, $10^4$, $10^5$, $10^6$, $10^7$, $10^8$, $10^9$, $10^{10}$, $10^{11}$, $10^{12}$, $10^{13}$, or any range or value therein, of fusion peptides or proteins.

A related embodiment describes a fusion protein comprising first and second polypeptides expressed from an engineered pIX phage vector of the invention, wherein the first polypeptide is an exogenous protein and the second polypeptide is a filamentous phage pVII or pIX protein, wherein the exogenous protein is fused to the amino terminus of the filamentous phage protein.

Still further, the invention contemplates a variety of methods for expressing proteins or peptides expressed from an engineered pIX phage vector of the invention, for producing a combinatorial library of phage, including by cloning repertoires of genes encoding an exogenous polypeptide into a vector of the present invention, modifying the structure of the exogenous polypeptides in a library by mutagenesis, by random combination of populations of first and second fusion protein libraries, by target and affinity selection ("panning") to alter the diversity of a library, and the like.

The design of proteins with improved or novel functions is an important goal with a variety of medical, industrial, environmental, and basic research applications. Following the development of combinatorial non-antibody peptide or protein libraries using engineered pIX phage vectors, a powerful next step is the evolution toward artificial non-antibody peptide or protein constructs as well as other protein motifs in which dimeric species are native or might be functional.

The present invention addresses these challenges by providing a phage-display format using an engineered pIX phage vector for the construction of combinatorial polypeptide arrays in which pVII and/or pIX are utilized for the display of fusion proteins that express monomeric or dimeric peptide or protein species.

Inherent in the scope and power of the technology is the ability to display a variety of proteins that can engage in monomeric or dimeric interactions. These include not only non-antibody peptides or proteins, but also some enzymes, hormones and hormone receptors, and DNA-binding proteins. The display technology described herein can be used for combinatorial alteration of non-antibody peptide or protein framework regions and to reorganize and miniaturize the non-antibody peptide or protein structure or to display DNA binding proteins, such as repressors, as a library of heterodimers for selection against particular DNA sequences of clinical and therapeutic importance.

Thus the present technology provides for the display and selection of a library of peptides or proteins and combinatorial libraries in which members consist of monomeric, homodimeric or heterodimeric arrays.

It should be understood that both the foregoing general description and the following detailed description are exemplary and explanatory only and are not restrictive of the invention as claimed.

DETAILED DESCRIPTION OF THE INVENTION

The present invention provides engineered pIX phage vectors that can be used with pVII and pIX phage display for generating peptide or protein libraries using pIX from M13 phage, e.g., using mutagenesis or other diversity producing techniques, optionally with in line maturation, to provide an efficient and fast platform for peptide or protein and non-antibody peptide or protein fragment generation and selection of therapeutic non-antibody peptides or proteins. According to the present invention, hybrid phage vectors are provided that have been engineered to include a second recombinant pIX coding region linked to an upstream signal peptide and inducible promoter.

The present invention provides a hybrid vector for the display of peptides and proteins as fusions to pIX or pVII phage proteins for use in expressing such peptides or proteins as peptide or protein libraries for use, e.g., but not limited to screening, selection, engineering, maturation or other uses, e.g., providing potential therapeutic or diagnostic peptides or proteins. Because the regulatory and coding regions of the native gene IX overlap those of pVII and pVIII, simple fusions to the terminus of this gene would likely inactivate the phage (Hill and Petersen, J. of Virol. 44:32-46, 1982) (8). Instead, a derivative of M13mp19 has been engineered to include a second recombinant pIX coding region linked to an upstream signal peptide and inducible promoter. The use of this vector, rather than a phagemid, obviates the need for helper phage and significantly reduces the amount of time and effort needed to culture the phage during selection and analysis. Furthermore, the number of phage grown with this vector can be determined more easily than the number of phage grown from a phagemid.

Thus the invention provides a novel vector construct for use in expressing peptides or proteins in a pIX phage display format for construction of polypeptide arrays. In particular, the invention describes an engineered pIX phage vector that includes a second recombinant pIX coding sequence encoding a fusion polypeptide, wherein the fusion polypeptide comprises an exogenous polypeptide fused to the amino terminus of a filamentous phage pVII or pIX protein. Preferably, the phage particle comprises the expressed fusion protein on the surface of the phage particle.

The human peptide or protein de novo library generated using such engineered pIX phage vectors described herein is distinct from current non-antibody peptide or protein library state-of-the-art by its displaying via pIX gene of M13 phage.

Filamentous Phage

The present invention contemplates using engineered pIX phage vectors as described herein with a pIX or pVII phage encoding at least one recombinant fusion peptide or protein. The fusion protein comprises an exogenous polypeptide portion fused to the amino terminus of a filamentous phage pVII or pIX protein.

By "exogenous" is meant that the polypeptide fused to the phage protein is not normally associated with the phage pVII or pIX protein in wild-type varieties of filamentous phage, but rather are foreign to the normal phage protein.

In a preferred embodiment, a filamentous phage encapsulates a genome which encodes a first and/or second fusion protein, where the first fusion protein comprises a first exogenous polypeptide fused to pVII or pIX and the second fusion protein comprises a second exogenous polypeptide fused to pIX or pIX.

The filamentous phage will further contain the fusion protein(s) displayed on the surface of the phage particle, as described herein. Thus, where there are at least first and second fusion proteins, the phage can display these proteins in a functional manner such that the first and second exogenous polypeptides can interact as a heterodimer to form a functional two-chain protein complex on the phage surface.

In a fusion protein present on a phage of this invention, the "fusion" between the exogenous polypeptide and the filamentous phage pVII or pIX protein can comprise a typical amide linkage, or can comprise a linker polypeptide (i.e., a "linker") as described in the Examples. Any of a variety of linkers can be used which are typically a stretch of about 5 to 50 amino acids in length. Particularly preferred linkers provide a high degree of mobility to the fusion protein at the point of the linker.

Library design: prior synthetic libraries have incorporated some of the following, but none have included all in a comprehensive manner.

Position and nature of sequence diversity. Sequence diversity is a hallmark of how human proteins are provided endogenously that provide high-affinity, selective binding entities. This generation and accumulation of sequence diversity is not random. The site and type of nucleotide mutations of genomic sequences are biased by DNA sequence and mechanism but only mutations that provide binding and functional advantage are selected and stored, often along with neutral substitutions. While not amenable to prediction from mechanism, databases of known human peptide or protein sequences and structure-function analysis identifies positions and amino substitutions most frequently associated with recognition of a desired target or antigen, including differentiation between protein, peptide and small molecule antigens. The libraries of the present invention provide this natural human diversity by utilizing designed degenerate oligonucleotides to incorporate substitutions into putative binding regions and functional areas of the peptide or protein sequences that are expressed.

Expression, biochemical, and biophysical properties. Preferred human non-antibody peptides or proteins have desired biological and binding activities, but also are efficiently produced from a variety of hosts, are stable, and have good solution properties. High-frequency germline gene usage (1d) also indicates good expression in mammalian systems. In addition, non-antibody peptides or proteins recovered from libraries by bacterial phage display methods of selection or screening should be expressed well in the bacterial host. The libraries of the invention are based on human germline derived templates that are well-expressed and purified from standard recombinant mammalian hosts (e.g. HEK 293 and CHO cells) as well as bacterial hosts, and have high stability and good solution properties.

Library assembly technologies. Preferred de novo non-antibody peptide or protein libraries are of high diversity ($>10^{10}$), amenable to alteration, and easy to assemble and have a low background of undesired sequences. These background sequences include parental template and low-targeted diversity. Coupling the following methods accelerates library assembly and leads to low background. (a) Kunkle-based single-stranded mutagenesis; (b) Palindromic loop with restriction site; (c) Megaprimer pIX peptide or protein phage display. All prior filamentous de novo human non-antibody peptide or protein libraries utilize pIII or pVIII phage coat proteins for display. The combination of pIX with the selected Peptide or protein templates is a more efficient selection system for recovering non-antibody peptides or proteins that retain their selected properties upon conversion into mAbs and other related molecules.

Peptide or protein display. Peptide or proteins are natural segments of human non-antibody peptides or proteins and they better recapitulate their activity when engineered into full non-antibody peptides or proteins. Efficient filamentous display of peptide or proteins can require properties beyond good expression in the bacterial host. Peptide sequences used on libraries of present invention were chosen for efficient display by pIX on filamentous phage.

Phagemid display. The peptide or protein molecule may be large relative to the phage pIX coat protein and thus can interfere with assembly of recombinant phage particles if linked to all pIX proteins produced in the bacterial cell. One approach to by-pass this interference is to use a pIX phagemid system, whereby both wild-type and peptide or protein-linked pIX proteins can be incorporated into the recombinant phage particle. In a preferred application, libraries of the present invention are displayed by pIX in a phagemid system.

Phage coat protein pIX for display. Like pIII, pIX is present at low copy number on the phage and is amenable to affinity selection of displayed peptide or proteins. However, the pIII protein is critically involved in the infection process and proteins displayed on this protein can interfere with the efficiency of infection. Moreover, either the heavy chain Fd or light chain segments can be fused to pIX for display. The libraries of the present invention displayed on the pIX protein are predicted to be efficiently replicated and presented for selection and/or screening.

Peptide or protein-pIX expression. One approach to screening peptide or proteins recovered from phage libraries is to remove the phage coat protein that is linked to the peptide or protein molecule for display. The small size of the pIX protein provides the option of production of screening of peptide or proteins directly without this step.

Phage construction. Suitable M13 or similar types of phage vectors can be used as engineered according to the present invention. Such vectors that encode pIX or pVII fusion proteins with suitable regulatory, selection, restriction and other needed sites and sequences (e.g., promoters, signal sequences, leaders (e.g., pelB), ribosome binding sites (e.g., Shine-Delgano), tags (e.g., FLAG tag); transcriptional terminator (e.g., trpA), selection (e.g., LACZ), restriction sites (e.g., HindIII, EcoRI), peptide linkers, and the like) are modified according to known techniques to also include a second pIX and/or pVII coding sequence linked to an upstream signal peptide encoding sequence and an inducible promoter (e.g., LacZa). This engineering obviates the need for a helper phage and also significantly reduces the time and effort needed to culture or grow the phage during the selection and/or analysis steps. Additionally, the number of phage needed to be groan can be determined more easily than using other vectors.

Figure 1:
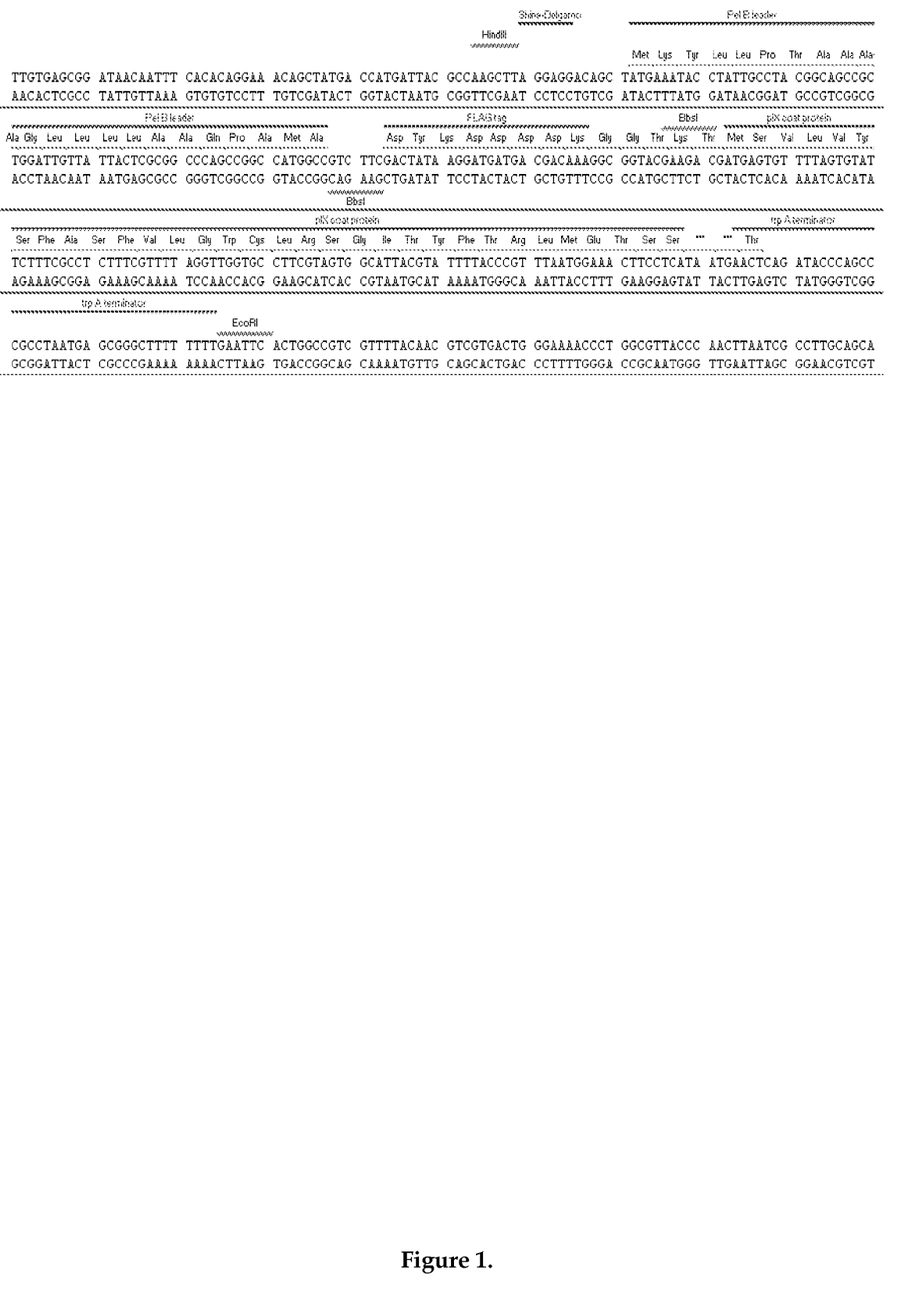
FIG. 1. Synthetic DNA insert for the expression of recombinant FLAG tag-pIX fusion protein in the M13-99 vector.

As a non-limiting example, M13KE, a derivative of M13mp19, are known phage vectors that can be used to provide an engineered pIX phage vector of the present invention by inserting a recombinant pIX gene. The recombinant region can be inserted, e.g., into the lacZα region of M13mp19, in the intergenic region of the phage genome, and thus the lac promoter drives transcription of the recombinant gene IX fusion. The insert (FIG. 1) can include a Shine- Delgarno sequence (ribosome-binding site), a signal sequence from pectate lyase B (pelB), dual BbsI restriction enzyme recognition sites for future cloning, the pIX coding region, and the trpA transcriptional terminator. A FLAG tag peptide DYKDDDDK and a five-amino acid linker (M13-99: GGTKT) or a nine-amino acid linker (M13-99L: SGGSG-GTKT) included between pelB and gene IX.

Additional peptides (e.g., but not limited to those in Table 1) with various lengths and charges can be displayed on the amino terminus of pIX with the nine-amino acid linker to determine which linker are most suitable for expressing a particular polypeptide. In addition, one or more exogenous fusion peptides are displayed on pIX or pVII.

The final phage vector can be analyzed containing the recombinant pIX genes for display of peptide tags, e.g., in ELISA experiments. Phages that bound to immobilized target peptides or proteins can be detected with an anti-M13/target conjugate or any other detection of the express exogenous peptide.

Advantages. The hybrid system for display of peptides on pIX offers advantages of speed and convenience over the previously developed pIX phagemid systems. Phage can be infected into host cells and amplified in an afternoon, essentially in a single step. Amplification of phagemid, by contrast, requires infection and outgrowth of the phagemid, superinfection with helper phage at a defined culture density, and amplification of rescued phage. The procedure thus entails additional steps and operator input and—at a minimum—an overnight culture. Over the course of the repeated selection cycles and multiple rounds of screening involved in a typical selection experiment, the time savings of a hybrid system can be significant. Furthermore, phagemid amplification generates a mixture of phage that contains either the phagemid or the helper phage genome. It is therefore more difficult to accurately quantitate the number of viral particles containing the phagemid genome. Since the hybrid system abolishes the need for helper phage infection only one type of phage genome is present that can be packaged into a phage particle. This generates a homogeneous population of phage allowing a precise measurement of viral particles containing the fusion genome.

While having described the invention in general terms, the embodiments of the invention will be further disclosed in the following examples that should not be construed as limiting the scope of the claims.

EXAMPLE 1

Exemplary Engineered Phage Vector Construction

Phage construction. M13-99 and M13-99L contain a recombinant pIX gene inserted into the phage genome M13KE, a derivative of M13mp19. The recombinant region has been inserted into the lacZα region of M13mp19, in the intergenic region of the phage genome, and thus the lac promoter drives transcription of the recombinant gene IX fusion. The insert (FIG. 1) included a Shine-Delgarno sequence (ribosome-binding site), a signal sequence from pectate lyase B (pelB), dual BbsI restriction enzyme recognition sites for future cloning, the pIX coding region, and the trpA transcriptional terminator. A FLAG tag peptide DYKDDDDK (SEQ ID NO:2) and a five-amino acid linker (M13-99: GGTKT (SEQ ID NO:7)) or a nine-amino acid linker (M13-99L: SGGSGGTKT (SEQ ID NO:8)) was included between pelB and gene IX.

Four additional peptides (Table 1) with various lengths and charges were displayed on the amino terminus of pIX with the nine-amino acid linker. In addition, epidermal growth factor (EGF) (5.6 kDa) was displayed on pIX to evaluate the feasibility of displaying a globular protein with multiple disulfide bonds.

Figure 2:
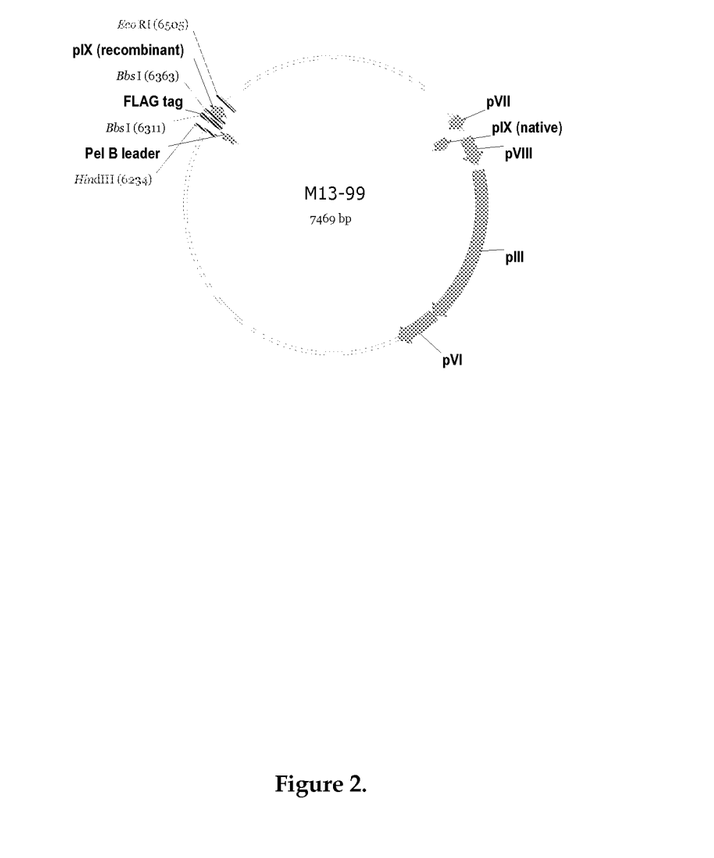
FIG. 2. Map of M13-99 showing the locations of native phage coat protein genes and the inserted recombinant pIX gene.

Methods. The DNA encoding the FLAG cassette (FIG. 1), flanked by HindIII and EcoRI enzyme recognition sites, was synthesized (Blue Heron), liberated from its shuttle vector by restriction enzyme digestion, and ligated into M13KE (New England Biolabs) that had been digested with HindIII and EcoRI. The final phage vector, M13-99 (SEQ ID NO. 1), is diagrammed in FIG. 2. For the other peptides, complimentary oligos were annealed together to generate appropriate DNA sequences. Annealed oligos contained compatible overhangs corresponding to the BbsI-digested M13-99L vector allowing for ligation of the peptide tag DNA and the vector. EGF was PCR amplified, digested with BbsI restriction endonuclease, and ligated into the BbsI digested M13-99L. Recombinant phages were plated to isolate single plaques on a lawn of XL-1 Blue host E. coli cells (Stratagene). Phage plaques were resuspended in media, and the phages were allowed to diffuse from the agar. The phages were infected into XL-1 Blue and cultured for 4.5 hr at 37° C. One mM IPTG was the standard means of inducing expression of the pIX fusion protein, but for some experiments various amounts of IPTG (1.0 to 0.01 mM) were used to induce the expression of EGF. After phage growth and induction, bacteria were removed by centrifugation, and the phage were precipitated from the culture supernatant with 4% PEG-8000, 0.5 M NaCl and incubation at 4° C. overnight. The phage particles were recovered by centrifugation, and the phage pellet was resuspended in phosphate-buffered saline (PBS).

Figure 3:
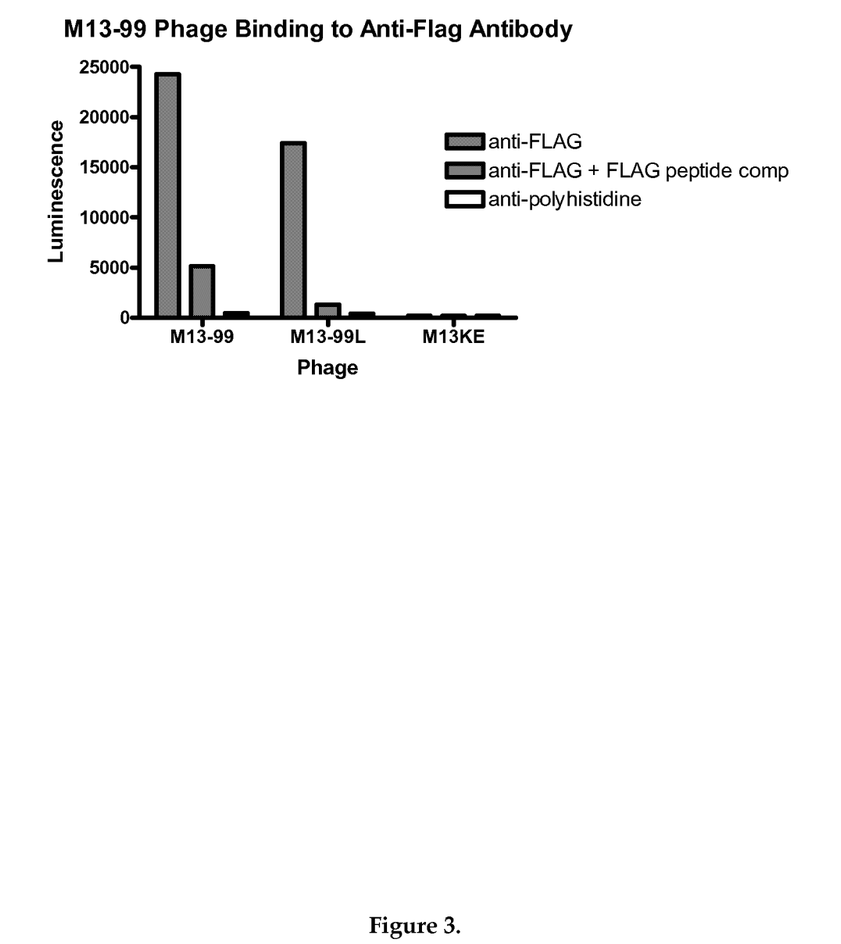
FIG. 3. ELISA showing specific binding of an anti-FLAG tag antibody to FLAG-pIX fusion proteins displayed on M13-99 and M13-99L phage.

Analysis of pIX-displayed peptides. The phages containing the recombinant pIX genes were tested for display of the peptide tags in ELISA experiments. Phages that bound to immobilized monoclonal non-antibody peptides or proteins were detected with an anti-M13/HRP conjugate. Besides M13-99 and M13-99L, the M13KE parent vector was included as a negative control. In duplicate anti-FLAG-coated wells, excess synthetic FLAG peptide was included in the phage binding reaction as a competitor. Both M13-99 and M13-99L were seen to bind specifically to the anti-FLAG antibody versus the anti-polyhistidine antibody, and this binding was inhibited with excess FLAG peptide, indicating successful display of the FLAG tag on the recombinant pIX (FIG. 3). M13-99L provided a lower background signal, and thus was used for the display of the other peptides.

Figure 4:
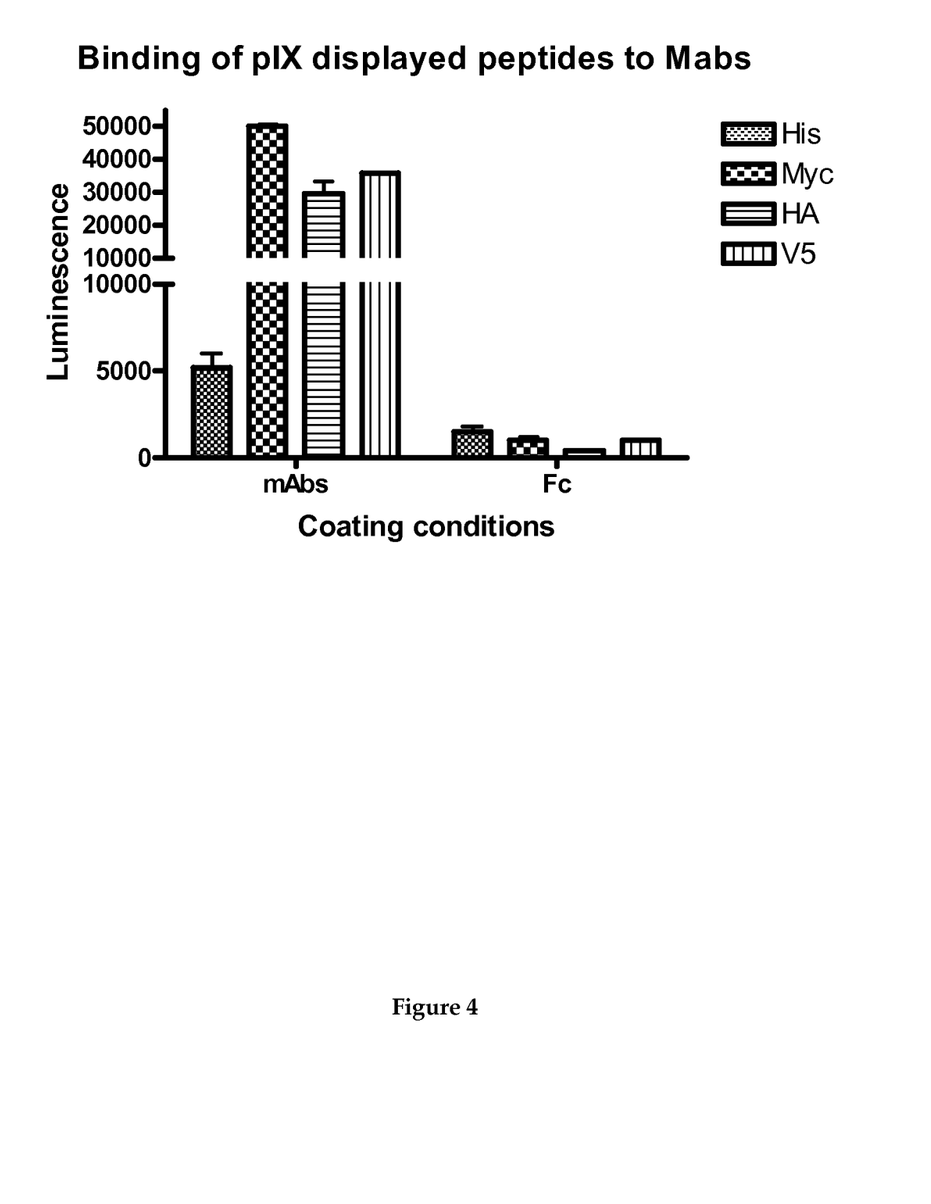
FIG. 4. Peptide epitopes displayed on pIX detected by ELISA.

The ELISA data for the other peptides are shown in FIG. 4. Anti-his, anti-myc, anti-V5 and anti-HA non-antibody peptides or proteins were used for the appropriate phage. Fc was included as a negative control in each experiment. These results indicate that these peptides were also successfully displayed on the recombinant pIX.

Methods. Wells of a Maxisorp ELISA plate (NUNC) were coated with 250 ng of monoclonal non-antibody peptides or proteins at 4 µg/ml in PBS, overnight at 4° C. The wells were rinsed twice with Tris-buffered saline containing 0.1% Tween-20 (TBS-T) and blocked with Starting Block (Pierce) for 1 hr at room temperature. The wells were rinsed again. PEG-precipitated phage (~$10^9$ pfu), diluted in Starting Block, were added to the wells and incubated for 1.5 hr at room temperature with shaking. For M13-99 and M13-99L, FLAG peptide was added to a final concentration of 0.1 mg/ml as a competitor and incubation was continued for 15 min. The wells were rinsed thrice with TBS-T, and anti-M13/horseradish peroxidase conjugate (GE Healthcare), diluted 1:5000 in Starting Block, was added to the wells and incubated for 1 hr at room temperature with shaking. The wells were rinsed thrice with TBS-T, and POD chemiluminescent substrate (Roche) was added and detected on a Tecan plate reader.

Figure 5:
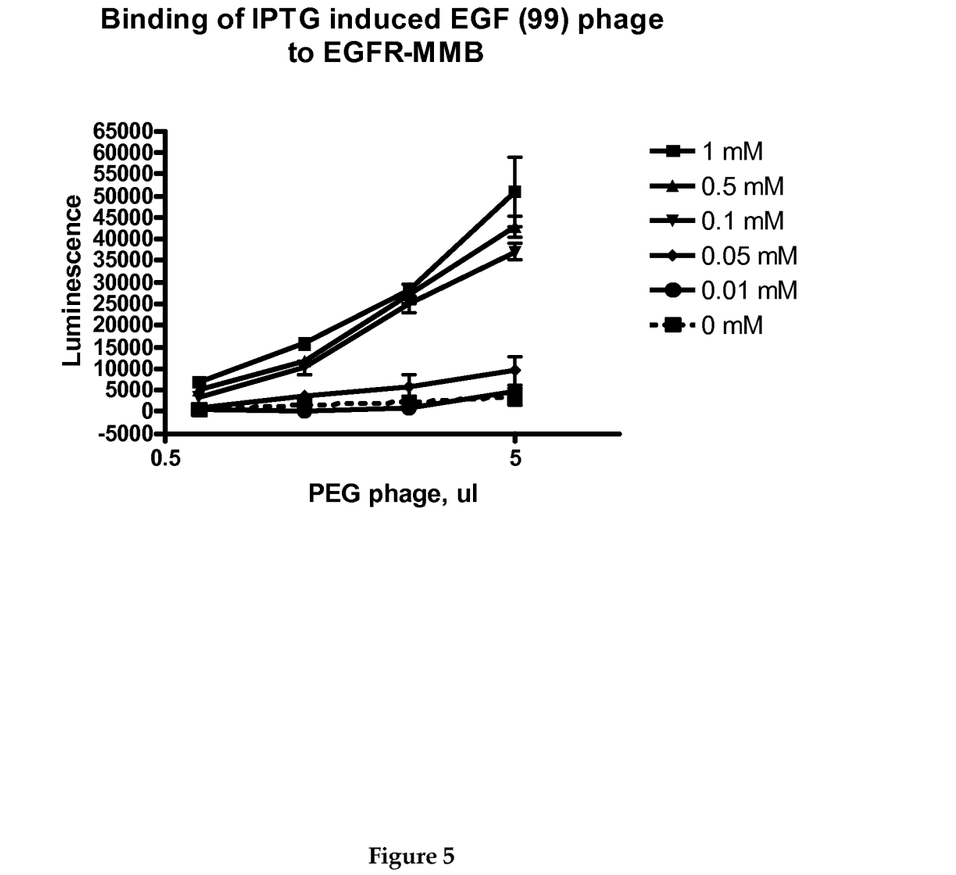
FIG. 5. EGF displayed on pIX detected by ELISA. Expression of EGF-pIX from the hybrid vector was induced by the addition of IPTG (0.01 mM-1 mM). Specific binding to EGFR-MMB is evident at [IPTG]>0.05 mM.
Figure 6:
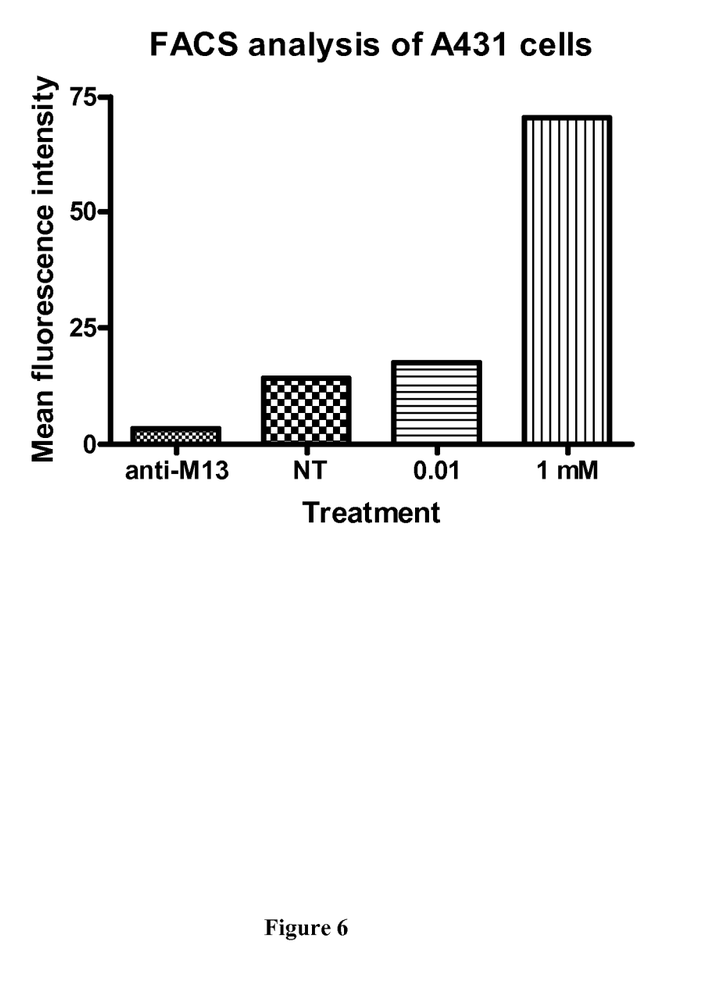
FIG. 6. FACS analysis of EGF displayed on pIX. Phagemid: EGF-pIX displayed in a phagemid system; NT: hybrid containing the pIX-EGF fusion grown without IPTG induction; 0.01 mM and 1 mM: EGF-pIX hybrid induced with 0.01 mM and 1 mM IPTG, respectively.

Analysis of pIX-displayed EGF. The binding of the pIX-displayed EGF to EGFR-MMB was tested in ELISA experiments and the binding to EGFR expressed on A431 cells was tested in FACS experiments. (Note that the EGFR-MMB fusion protein has been described in another recent invention disclosure.) Phage particles that bound to EGFR-MMB by ELISA were detected with an anti-m13:HRP Mab (FIG. 5), while those that bound to EGFR on A431 cells by FACS were detected with an anti-M13:FITC Mab (FIG. 6). The ELISA data demonstrated that EGF was successfully displayed in the pIX hybrid system. In the FACS experiments, the parental vector M13KE and uninduced EGF—pIX hybrid phage were included as negative controls. Methods. For ELISA experiments, Maxisorp plates were coated with 5 µg/mL of anti-Fc mAb overnight at 4° C. The plates were washed three times with TBS-T followed by the addition of 500 ng of EGFR-MMB to half of the coated wells. The remaining wells were treated with TBS-T. Plates were washed and blocked with 300 µl/well Chemiblocker (Chemicon) for 1 hour at room temperature. The wells were washed with TBS-T, serial dilutions of the phage were added to the wells, and were allowed to bind for 1 hour. After washing the wells 3 times with TBS-T, bound phage were detected as described above. For FACS analysis, A431 cells were harvested with 0.25% tyrpsin-EDTA, washed twice with complete DMEM containing 10% FBS and 1% NEAA, and resuspended at 2.5×10⁶ cells/mL in FACS buffer containing sodium azide. Cells (2.5×10⁵) were incubated with titer equivalent quantities of phage, or mouse anti-M13:FITC (RDI, Fitzgerald Industries) for one hour at 4° C. in FACS buffer containing sodium azide. Cells were washed twice in FACS buffer to remove any unbound phage and were incubated with mouse anti-M13:FITC antibody for one hour at 4° C. in FACS buffer. Cells were washed to remove unbound antibody and phage binding was analyzed by flow cytometry.

TABLE 1

Peptide sequences cloned into the pIX hybrid expression vector.

| Peptide tags | Amino acid sequence | |
|---|---|---|
| FLAG | DYKDDDDK | (SEQ ID NO: 2) |
| HA | YPYDVPDYA | (SEQ ID NO: 3) |
| HIS | HHHHHH | (SEQ ID NO: 4) |
| MYC | MEQKLISEEDLNS | (SEQ ID NO: 5) |
| V5 | GKPIPNPLLGLDST | (SEQ ID NO: 6) |

References

1. Kehoe, J. W., and B. K. Kay. 2005. Filamentous phage display in the new millennium. Chem Rev 105:4056.
2. Iannolo, G., O. Minenkova, R. Petruzzelli, and G. Cesareni. 1995. Modifying filamentous phage capsid: limits in the size of the major capsid protein. J Mol Biol 248:835.
3. Gao, C., S. Mao, C. H. Lo, P. Wirsching, R. A. Lerner, and K. D. Janda. 1999. Making artificial non-antibody peptides or proteins: a format for phage display of combinatorial heterodimeric arrays. Proc Natl Acad Sci USA 96:6025.
4. Gao, C., S. Mao, G. Kaufmann, P. Wirsching, R. A. Lerner, and K. D. Janda. 2002. A method for the generation of combinatorial antibody libraries using pIX phage display. Proc Natl Acad Sci USA 99:12612.
5. Gao, C., S. Mao, H. J. Ditzel, L. Farnaes, P. Wirsching, R. A. Lerner, and K. D. Janda. 2002. A cell-penetrating peptide from a novel pVII-pIX phage-displayed random peptide library. Bioorg Med Chem 10:4057.
6. Endemann, H., and P. Model. 1995. Location of filamentous phage minor coat proteins in phage and in infected cells. J Mol Biol 250:496.
7. Kwasnikowski, P., P. Kristensen, and W. T. Markiewicz. 2005. Multivalent display system on filamentous bacteriophage pVII minor coat protein. J Immunol Methods 307:135.
8. Hill, D. F., and G. B. Petersen. 1982. Nucleotide Sequence of Bacteriophage f1DNA. Journal of Virology 44:32.

What is claimed:

1. An engineered recombinant nucleic acid phage hybrid vector for expressing phage displayed fusion peptides or proteins that bind to selected biologically active ligands, comprising
   a. a recombinant Pel B phage leader coding nucleic acid sequence; operably linked to:
   b. a recombinant tag, promoter, or selection coding nucleic acid sequence; operably linked to:
   c. a recombinant pIX encoding nucleic acid sequence; operably linked to:
   d. a recombinant restriction site; operably linked to:
   e. a peptide linker encoding nucleic acid sequence; operably linked to a:
   f. a first exogenous peptide or protein encoding sequence that selectively binds to a biologically active ligand, wherein said first exogenous peptide or protein encoding sequence is fused to said recombinant pIX encoding nucleic acid sequence; and
   g. a pVII encoding nucleic acid sequence;
   h. a native pIX encoding nucleic acid sequence;
   i. a pIII encoding nucleic acid sequence; and a pVI encoding nucleic acid sequence,
   wherein said vector encodes a second exogenous peptide or protein fused to a phage coat protein selected from pVII and pIII,
   wherein said phage hybrid vector expresses functional forms of said first exogenous peptide or protein and said second exogenous peptide or protein in a bacterial host cell system without the use of helper phage.

2. An engineered nucleic acid phage hybrid vector according to claim 1, wherein said recombinant tag or selection coding nucleic acid sequence is a FLAG tag sequence.

3. An nucleic acid phage hybrid vector according to claim 1, wherein said recombinant tag or selection coding nucleic acid sequence is selected from SEQ ID NOS:3, 4, 5, or 6.

4. An engineered nucleic acid phage hybrid vector according to claim 2, wherein said FLAG tag sequence comprises SEQ ID NO:2.

5. An engineered nucleic acid phage hybrid vector according to claim 1, wherein said promoter is an inducible promoter.

6. An engineered nucleic acid phage hybrid vector according to claim 5, wherein said inducible promoter is a lac promoter.

7. An engineered nucleic acid phage hybrid vector according to claim 1, wherein said peptide linker is selected from SEQ ID NOS:7 and 8.

8. An engineered nucleic acid phage hybrid vector to claim 1, wherein said first exogenous peptide or protein is a putative biologically active proteins or peptides.

9. An engineered nucleic acid phage hybrid vector according to claim 8, wherein said biologically active proteins or peptides mediate at least one biological in vivo activity.

10. A bacterial host cell comprising an engineered nucleic acid phage hybrid vector according to claim 1.

11. A phage library of bacterial host cells comprising a plurality of engineered nucleic acid phage hybrid vectors according to claim 1.

12. A phage library according to claim 11, wherein variants of said exogenous first peptides or proteins are expressed.

* * * * *

UNITED STATES PATENT AND TRADEMARK OFFICE
CERTIFICATE OF CORRECTION

Page 1 of 1

PATENT NO. : 8,728,982 B2
APPLICATION NO. : 12/743249
DATED : May 20, 2014
INVENTOR(S) : Bryan Wang, Linus Hyun and Karyn O'Neil It is certified that error appears in the above-identified patent and that said Letters Patent is hereby corrected as shown below:

ON THE TITLE PAGE:

Column 1, after paragraph (65), please add:

-- Related U.S. Application Data (60) Provisional application No. 61/014,773, filed Dec. 19, 2007. --

Signed and Sealed this
Seventh Day of April, 2015

Michelle K. Lee
*Director of the United States Patent and Trademark Office*

SEQUENCE LISTING

<160> NUMBER OF SEQ ID NOS: 8

<210> SEQ ID NO 1
<211> LENGTH: 7469
<212> TYPE: DNA
<213> ORGANISM: homo sapien

<400> SEQUENCE: 1

```
aatgctacta ctattagtag aattgatgcc accttttcag ctcgcgcccc aaatgaaaat      60
atagctaaac aggttattga ccatttgcga aatgtatcta atggtcaaac taaatctact     120
cgttcgcaga attgggaatc aactgttaca tggaatgaaa cttccagaca ccgtacttta     180
gttgcatatt taaacatgt tgagctacag caccagattc agcaattaag ctctaagcca     240
tccgcaaaaa tgacctctta tcaaaaggag caattaaagg tactctctaa tcctgacctg     300
```

```
ttggagtttg cttccggtct ggttcgcttt gaagctcgaa ttaaaacgcg atatttgaag    360
tctttcgggc ttcctcttaa tcttttgat gcaatccgct ttgcttctga ctataatagt    420
cagggtaaag acctgatttt tgatttatgg tcattctcgt tttctgaact gtttaaagca   480
tttgaggggg attcaatgaa tatttatgac gattccgcag tattggacgc tatccagtct   540
aaacatttta ctattacccc ctctggcaaa acttcttttg caaaagcctc tcgctatttt   600 ggttttatc gtcgtctggt aaacgagggt tatgatagtg ttgctcttac tatgcctcgt    660
aattcctttt ggcgttatgt atctgcatta gttgaatgtg gtattcctaa atctcaactg   720
atgaatcttt ctacctgtaa taatgttgtt ccgttagttc gttttattaa cgtagatttt   780
tcttcccaac gtcctgactg gtataatgag ccagttctta aaatcgcata aggtaattca   840
caatgattaa agttgaaatt aaaccatctc aagcccaatt tactactcgt tctggtgttt   900
ctcgtcaggg caagccttat tcactgaatg agcagctttg ttacgttgat ttgggtaatg   960
aatatccggt tcttgtcaag attactcttg atgaaggtca gccagcctat gcgcctggtc   1020
tgtacaccgt tcatctgtcc tctttcaaag ttggtcagtt cggttcccct atgattgacc   1080
gtctgcgcct cgttccggct aagtaacatg gagcaggtcg cggatttcga cacaatttat   1140
caggcgatga tacaaatctc cgttgtactt tgtttcgcgc ttggtataat cgctggggt    1200 caaagatgag tgttttagtg tattcttccg cctctttcgt tttaggttgg tgccttcgta   1260
gtggcattac gtattttacc cgtttaatgg aaacttcctc atgaaaaagt ctttagtcct   1320
caaagcctct gtagccgttg ctaccctcgt tccgatgctg tctttcgctg ctgagggtga   1380
cgatcccgca aaagcggcct ttaactccct gcaagcctca gcgaccgaat atatcggtta   1440
tgcgtgggcg atggttgttg tcattgtcgg cgcaactatc ggtatcaagc tgtttaagaa   1500
attcacctcg aaagcaagct gataaaccga tacaattaaa ggctcctttt ggagcctttt   1560
ttttggagat ttcaacgtg aaaaaattat tattcgcaat tcctttagtg gtacctttct    1620
attctcactc ggccgaaact gttgaaagtt gtttagcaaa atcccataca gaaaattcat   1680
ttactaacgt ctggaaagac gacaaaactt tagatcgtta cgctaactat gagggttgtc   1740
tgtggaatgc tacaggcgtt gtagtttgta ctggtgacga aactcagtgt tacggtacat   1800
gggttcctat tgggcttgct atccctgaaa atgagggtgg tggctctgag ggtggcggtt   1860
ctgagggtgt cggttctgag ggtggcggta ctaaacctcc tgagtacggt gatacaccta   1920
ttccgggcta tacttatatc aaccctctcg acggcactta tccgcctggt actgagcaaa   1980
accccgctaa tcctaatcct tctcttgagg agtctcagcc tcttaatact ttcatgtttc   2040
agaataatag gttccgaaat aggcaggggg cattaactgt ttatacgggc actgttactc   2100
aaggcactga ccccgttaaa acttattacc agtacactcc tgtatcatca aaagccatgt   2160
atgacgctta ctggaacggt aaattcagag actgcgcttt ccattctggc tttaatgaag   2220
atccattcgt ttgtgaatat caaggccaat cgtctgacct gcctcaacct cctgtcaatg   2280
ctggcggcgg ctctggtggt ggttctggtg cggctctga gggtggtggc tctgagggtg    2340
gcggttctga gggtggcggc tctgaggag gcggttccgg tggtggctct ggttccggtg    2400
attttgatta tgaaaagatg gcaaacgcta ataagggggc tatgaccgaa atgccgatg    2460 aaaacgcgct acagtctgac gctaaaggca aacttgattc tgtcgctact gattacggtg   2520
ctgctatcga tggtttcatt ggtgacgttt ccggccttgc taatggtaat ggtgctactg   2580
gtgattttgc tggctctaat tcccaaatgg ctcaagtcgg tgacggtgat aattcacctt   2640
taatgaataa tttccgtcaa tatttacctt ccctccctca atcggttgaa tgtcgccctt   2700
```

```
ttgtctttag cgctggtaaa ccatatgaat tttctattga ttgtgacaaa ataaacttat    2760
tccgtggtgt ctttgcgttt cttttatatg ttgccacctt tatgtatgta ttttctacgt    2820
ttgctaacat actgcgtaat aaggagtctt aatcatgcca gttcttttgg gtattccgtt    2880
attattgcgt ttcctcggtt tccttctggt aactttgttc ggctatctgc ttacttttct    2940
taaaaagggc ttcggtaaga tagctattgc tatttcattg tttcttgctc ttattattgg    3000
gcttaactca attcttgtgg gttatctctc tgatattagc gctcaattac cctctgactt    3060
tgttcagggt gttcagttaa ttctcccgtc taatgcgctt ccctgttttt atgttattct    3120
ctctgtaaag gctgctattt tcattttga cgttaaacaa aaaatcgttt cttatttgga    3180 tgggataaa taatatggct gtttattttg taactggcaa attaggctct ggaaagacgc    3240
tcgttagcgt tggtaagatt caggataaaa ttgtagctgg gtgcaaaata gcaactaatc    3300
ttgatttaag gcttcaaaac ctcccgcaag tcgggaggtt cgctaaaacg cctcgcgttc    3360
ttagaatacc ggataagcct tctatatctg atttgcttgc tattgggcgc ggtaatgatt    3420
cctacgatga aaataaaaac ggcttgcttg ttctcgatga gtgcggtact tggtttaata    3480
cccgttcttg gaatgataag gaaagacagc cgattattga ttggtttcta catgctcgta    3540
aattaggatg ggatattatt tttcttgttc aggacttatc tattgttgat aaacaggcgc    3600
gttctgcatt agctgaacat gttgtttatt gtcgtcgtct ggacagaatt actttacctt    3660
ttgtcggtac tttatattct cttattactg gctcgaaaat gcctctgcct aaattacatg    3720
ttggcgttgt taaatatggc gattctcaat taagccctac tgttgagcgt tggctttata    3780
ctggtaagaa tttgtataac gcatatgata ctaaacaggc ttttttctagt aattatgatt    3840 ccggtgttta ttcttatta acgccttatt tatcacacgg tcggtatttc aaaccattaa    3900
atttaggtca gaagatgaaa ttaactaaaa tatatttgaa aaagttttct cgcgttcttt    3960
gtcttgcgat tggatttgca tcagcattta catatagtta tataacccaa cctaagccgg    4020
aggttaaaaa ggtagtctct cagacctatg attttgataa attcactatt gactcttctc    4080
agcgtcttaa tctaagctat cgctatgttt tcaaggattc taagggaaaa ttaattaata    4140
gcgacgattt acagaagcaa ggttattcac tcacatatat tgatttatgt actgtttcca    4200
ttaaaaaagg taattcaaat gaaattgtta aatgtaatta attttgtttt cttgatgttt    4260
gtttcatcat cttcttttgc tcaggtaatt gaaatgaata attcgcctct gcgcgatttt    4320
gtaacttggt attcaaagca atcaggcgaa tccgttattg tttctcccga tgtaaaaggt    4380
actgttactg tatattcatc tgacgttaaa cctgaaaatc tacgcaattt ctttatttct    4440
gttttacgtg ctaataattt tgatatggtt ggttcaattc cttccataat tcagaagtat    4500
aatccaaaca atcaggatta tattgatgaa ttgccatcat ctgataatca ggaatatgat    4560
gataattccg ctccttctgg tggtttcttt gttccgcaaa atgataatgt tactcaaact    4620
tttaaaatta ataacgttcg ggcaaaggat ttaatacgag ttgtcgaatt gtttgtaaag    4680
tctaatactt ctaaatcctc aaatgtatta tctattgacg gctctaatct attagttgtt    4740
agtgcaccta agatatttt agataacctt cctcaattcc tttctactgt tgatttgcca    4800
actgaccaga tattgattga gggtttgata tttgaggttc agcaaggtga tgctttagat    4860
ttttcatttg ctgctggctc tcagcgtggc actgttgcag cgggtgttaa tactgaccgc    4920
ctcacctctg ttttatcttc tgctggtggt tcgttcggta tttttaatgg cgatgtttta    4980
gggctatcag ttcgcgcatt aaagactaat agccattcaa aaatattgtc tgtgccacgt    5040
attcttacgc tttcaggtca gaagggttct atctctgttg gccagaatgt ccctttatt    5100
```

```
actggtcgtg tgactggtga atctgccaat gtaaataatc catttcagac gattgagcgt    5160
caaaatgtag gtatttccat gagcgttttt cctgttgcaa tggctggcgg taatattgtt    5220
ctggatatta ccagcaaggc cgatagtttg agttcttcta ctcaggcaag tgatgttatt    5280
actaatcaaa gaagtattgc tacaacggtt aatttgcgtg atggacagac tcttttactc    5340
ggtggcctca ctgattataa aaacacttct caagattctg gcgtaccgtt cctgtctaaa    5400
atccctttaa tcggcctcct gtttagctcc cgctctgatt ccaacgagga aagcacgtta    5460
tacgtgctcg tcaaagcaac catagtacgc gccctgtagc ggcgcattaa gcgcggcggg    5520
tgtggtggtt acgcgcagcg tgaccgctac acttgccagc gccctagcgc ccgctccttt    5580
cgctttcttc ccttcctttc tcgccacgtt cgccggcttt ccccgtcaag ctctaaatcg    5640 gggctccct ttagggttcc gatttagtgc tttacggcac ctcgacccca aaaaacttga    5700
tttgggtgat ggttcacgta gtgggccatc gccctgatag acggtttttc gccctttgac    5760
gttggagtcc acgttcttta atagtggact cttgttccaa actggaacaa cactcaaccc    5820
tatctcgggc tattcttttg atttataagg gattttgccg atttcggaac caccatcaaa    5880
caggattttc gcctgctggg gcaaaccagc gtggaccgct tgctgcaact ctctcagggc    5940
caggcggtga agggcaatca gctgttgccc gtctcgctgg tgaaaagaaa aaccaccctg    6000
gcgcccaata cgcaaaccgc ctctccccgc gcgttggccg attcattaat gcagctggca    6060
cgacaggttt cccgactgga aagcgggcag tgagcgcaac gcaattaatg tgagttagct    6120
cactcattag gcaccccagg ctttacactt tatgcttccg gctcgtatgt tgtgtggaat    6180
tgtgagcgga taacaatttc acacaggaaa cagctatgac catgattacg ccaagcttag    6240
gaggacagct atgaaatacc tattgcctac ggcagccgct ggattgttat tactcgcggc    6300
ccagccggcc atggccgtct tcgactataa ggatgatgac gacaaaggcg gtacgaagac    6360
gatgagtgtt ttagtgtatt cttcgcctc tttcgtttta ggttggtgcc ttcgtagtgg    6420
cattacgtat tttacccgtt taatgggaac ttcctcataa tgaactcaga tacccagccc    6480
gcctaatgag cgggcttttt tttgaattca ctggccgtcg ttttacaacg tcgtgactgg    6540
gaaaaccctg gcgttaccca acttaatcgc cttgcagcac atcccccttt cgccagctgg    6600
cgtaatagcg aagaggcccg caccgatcgc ccttcccaac agttgcgcag cctgaatggc    6660
gaatggcgct ttgcctggtt tccggcacca gaagcggtgc cggaaagctg gctggagtgc    6720
gatcttcctg aggccgatac ggtcgtcgtc ccctcaaact ggcagatgca cggttacgat    6780
gcgcccatct acaccaacgt aacctatccc attacggtca atccgccgtt tgttcccacg    6840
gagaatccga cgggttgtta ctcgctcaca tttaatgttg atgaaagctg gctacaggaa    6900
ggccagacgc gaattatttt tgatggcgtt cctattggtt aaaaaatgag ctgatttaac    6960
aaaaatttaa cgcgaatttt aacaaaatat taacgtttac aatttaaata tttgcttata    7020
caatcttcct gtttttgggg cttttctgat tatcaaccgg ggtacatatg attgacatgc    7080
tagttttacg attaccgttc atcgattctc ttgtttgctc cagactctca ggcaatgacc    7140
tgatagcctt tgtagatctc tcaaaaatag ctaccctctc cggcattaat ttatcagcta    7200
gaacggttga atatcatatt gatggtgatt tgactgtctc cggcctttct cacccttttg    7260
aatctttacc tacacattac tcaggcattg catttaaaat atatgagggt tctaaaaatt    7320
tttatccttg cgttgaaata aaggcttctc ccgcaaaagt attacagggt cataatgttt    7380
ttggtacaac cgatttagct ttatgctctg aggctttatt gcttaatttt gctaattctt    7440
tgccttgcct gtatgattta ttggatgtt                                      7469
```

```
<210> SEQ ID NO 2
<211> LENGTH: 8
<212> TYPE: PRT
<213> ORGANISM: homo sapien

<400> SEQUENCE: 2

Asp Tyr Lys Asp Asp Asp Asp Lys
 1               5

<210> SEQ ID NO 3
<211> LENGTH: 9
<212> TYPE: PRT
<213> ORGANISM: homo sapien

<400> SEQUENCE: 3

Tyr Pro Tyr Asp Val Pro Asp Tyr Ala
 1               5

<210> SEQ ID NO 4
<211> LENGTH: 6
<212> TYPE: PRT
<213> ORGANISM: homo sapien

<400> SEQUENCE: 4

His His His His His His
 1               5

<210> SEQ ID NO 5
<211> LENGTH: 13
<212> TYPE: PRT
<213> ORGANISM: homo sapien

<400> SEQUENCE: 5

Met Glu Gln Lys Leu Ile Ser Glu Glu Asp Leu Asn Ser
 1               5                  10

<210> SEQ ID NO 6
<211> LENGTH: 14
<212> TYPE: PRT
<213> ORGANISM: homo sapien

<400> SEQUENCE: 6

Gly Lys Pro Ile Pro Asn Pro Leu Leu Gly Leu Asp Ser Thr
 1               5                  10

<210> SEQ ID NO 7
<211> LENGTH: 5
<212> TYPE: PRT
<213> ORGANISM: homo sapien

<400> SEQUENCE: 7

Gly Gly Thr Lys Thr
 1               5

<210> SEQ ID NO 8
<211> LENGTH: 9
<212> TYPE: PRT
<213> ORGANISM: homo sapien

<400> SEQUENCE: 8

Ser Gly Gly Ser Gly Gly Thr Lys Thr
 1               5
```